(12) United States Patent
Distad

(10) Patent No.: US 6,932,213 B1
(45) Date of Patent: Aug. 23, 2005

(54) BABY TEETH COLLECTOR BOX WITH PILLOW TOOTHBOX

(76) Inventor: Elaine Sandra Fram Distad, P.O. Box 141, Cincinnatus, NY (US) 13040

(*) Notice: Subject to any disclaimer, the term of this patent is extended or adjusted under 35 U.S.C. 154(b) by 228 days.

(21) Appl. No.: 10/134,200

(22) Filed: Apr. 27, 2002

(51) Int. Cl.[7] .......... A61C 19/10; B65D 69/00; B65D 21/02; B65D 85/00

(52) U.S. Cl. .......... 206/83; 206/232; 220/23.87; 220/555

(58) Field of Search .......... 206/83, 368, 0.81, 206/0.84, 575, 579, 232, 457, 315.1, 533, 538; 220/23.83, 23.86, 23.87, 506, 507, 523, 553, 555, 796, 256.1, 258.1

(56) References Cited

U.S. PATENT DOCUMENTS

| | | | |
|---|---|---|---|
| 2,096,825 A | * | 10/1937 | Roman .......... 220/506 |
| 2,774,466 A | * | 12/1956 | Liska .......... 206/538 |
| 4,334,869 A | | 6/1982 | Wilcox et al. |
| 4,466,799 A | | 8/1984 | Argiro |
| D278,097 S | * | 3/1985 | Akiyoshi .......... D3/295 |
| D280,781 S | | 10/1985 | Zarganis |
| 4,694,956 A | | 9/1987 | Sims |
| 4,698,023 A | | 10/1987 | Marino |
| 4,775,318 A | * | 10/1988 | Breslin .......... 206/63.5 |
| 4,777,745 A | | 10/1988 | Rose |
| 4,846,692 A | | 7/1989 | Delcambre |
| 4,923,058 A | | 5/1990 | Dennison |
| 5,015,209 A | | 5/1991 | Ortiz |
| D325,281 S | * | 4/1992 | Jordan .......... D3/302 |
| 5,303,819 A | * | 4/1994 | Goldberg .......... 206/83 |
| 5,394,989 A | | 3/1995 | Delson |
| 5,501,602 A | | 3/1996 | Anderson et al. |
| 5,522,507 A | | 6/1996 | Cruz |
| 5,575,028 A | | 11/1996 | Brau et al. |
| 5,621,990 A | | 4/1997 | Blanchard |
| 5,989,035 A | | 11/1999 | Okoye |

OTHER PUBLICATIONS

A Beka Home School Catalogue 2001, p. 25, 58 Published by A Beka Book, Pensacola, FL, USA.

Satico's Parent Teacher Store 2002, Catalogue p. 62, 77, 80, 81. Published by McGraw Hill Children's Publishing. © 2002 Thoroughbred Catalogues.

Creative Educational Materials 2002 Catalog # 545 ©2001 by Triarco (located in Plymouth, MN).

* cited by examiner

Primary Examiner—Mickey Yu
Assistant Examiner—J. Gregory Pickett

(57) ABSTRACT

A receptacle (30) having multiple smaller compartments (42) for receiving baby teeth, and a larger compartment (74) for housing a smaller removable receptacle (56) used for placing a baby tooth under a child's pillow. Receptacle (30) comprises a floor (28) with upwardly extending peripheral outer sidewall (34) and slightly shorter partition walls (38) extending from outer sidewall (34) to inner sidewall (36) whose inner periphery forms larger compartment (74). Cover (48) closes the receptacle with a friction fit. Removable digram/date card(82) bears indicia representing twenty baby teeth and a line on which to write date of loss. Shield card (86) allows removal of one tooth for viewing.

9 Claims, 4 Drawing Sheets

BABY TEETH COLLECTOR BOX WITH PILLOW TOOTHBOX

FEDERALLY SPONSORED RESEARCH

Not Applicable

SEQUENCE LISTING OR PROGRAM

Not Applicable

BACKGROUND

1. Field of Invention

This invention relates generally to a collection/storage/educational receptacle and more specifically to a receptacle for the collection and storage of a child's baby teeth as well as the storage of a single tooth receiving receptacle.

BACKGROUND

2. Discussion of Prior Art

When my first child lost his first tooth at the age of seven, I looked for a small container in which to save it. Finding none on the market, I chose a small cardboard jewelry box. By the time my third child lost his first tooth, I still could find no container specifically designed to collect, store and display his teeth, so I resorted to placing it in a pill bottle.

Additionally, I wanted to find a very small container in which he could put his tooth in order to place it under his pillow for the "tooth fairy". I decided that since I could not find a container specifically designed to collect, organize and store baby teeth in addition to including a smaller container to hold a single tooth, I would have to invent one myself.

The need exists for a very simple, inexpensive, lightweight collection and storage container specifically designed for storing baby teeth and which includes a receptacle to receive a single tooth for placement under the child's pillow (henceforth called a pillow toothbox). Furthermore, the need exists for a teeth collection container with a storage compartment for the removable pillow toothbox. In addition, the need exists for the invention to include a removable device by which to record the date of each loss. I hope to see this invention on the market by the time my fourth child loses her first tooth.

Prior Art: U.S. Patent Tooth Receiving Receptacles

U.S. Pat. No. 5,501,602 to Anderson et al., 1996 Mar. 26, and U.S. Pat. No. 5,522,507 to Cruz, 1996 Jun. 4, are kits for enacting the tooth fairy fable, each containing multiple items. They involve a time-consuming effort to retrieve a child's tooth and to accomplish the illusion of the tooth fairy's existence.

Referring to No. 5,522,507, the first preferred embodiment of the kit's tooth storage container shown in FIG. 10 appears to hold only three teeth. The second preferred embodiment shown in FIG. 11 does not have a place on which to enter the date of loss. Additionally, though it closes on a hinge, it has no apparatus for securing closure nor does it have a friction fit. The kits are also much more complex and expensive to manufacture than a single collector box with removable pillow toothbox.

U.S. Pat. No. 4,923,058 to Dennison, 1990 May 8, is a tooth storage container but it contains no pillow toothbox or device by which to record the date of each loss. Additionally, it is built with a base containing pockets which is then inserted into the container body. This design includes a part which may be eliminated. This design is more complicated than a one-piece mold and adds another step to the manufacturing process.

U.S. Pat. No. 4,694,956 to Sims, 1987 Sep. 22, is a tooth storage container which looks like a large set of jaws. It is a relatively complex structure to manufacture.

Additionally, it does not contain a pillow toothbox or a device by which to record the date of each loss.

U.S. Pat. No. D280,781 to Zarganis, 1985 Oct. 1, is a storage case for baby teeth which looks like a giant tooth with wings. Though appropriate for a very young child, the grown teenager would not like to have a very juvenile looking keepsake container displayed on his dresser. If the parent desires to enact the tooth fairy fable, the collected teeth must be stored secretly to maintain the illusion of the tooth fairy's existence. Therefore, the stored teeth and container will not be presented to the child until he has lost all 20 teeth (at least a teenager) and would require a more mature looking keepsake box. This is also the disadvantage of numerous other design patents. A further disadvantage is that the invention does not include a pillow toothbox or device by which to record the date of loss.

U.S. Pat. No. 5,621,990 to Blanchard, 1997 Apr. 22, is a keepsake holder for baby teeth. However, it is a folded card with pockets for each tooth. This would not be as durable as a solid container of molded plastic. Also, the invention does not include a pillow toothbox.

U.S. Pat. No. 5,303,819 to Goldberg, 1994 Apr. 19, is a display holder for teeth. It contains no pillow toothbox. Furthermore, it is designed to be hung on the wall; therefore, it is not portable. Also, the record of loss is not removable.

U.S. Pat. No. 4,777,745 to Rose, 1988 Oct. 18, is a tooth storage and display apparatus. It comprises a picture frame with hidden compartments inside. However, it is complicated, costly, large, and comparatively expensive to manufacture. Furthermore, it consists of indentations for items used in the enactment of the tooth fairy fable but contains no pillow toothbox.

Single tooth receiving receptacles in the form of pillows, pouches and dolls exist in the prior art, but they have no multiple tooth receiving/storage receptacle in which to rest. This is a distinct disadvantage. These include the following: U.S. Pat. No. 5,575,028 to Brau et al., 1996 Nov. 19, is a cushion for holding a toothbrush and toothpaste and having a pocket to receive a single tooth. U.S. Pat. No. 5,015,209 to Ortiz, 1991 May 14, is a doll having a pouch to receive a single tooth. U.S. Pat. No. 5,394,989 to Delson, 1995 Mar. 7, is a castle containing a pouch to receive a single tooth. Without a complementary multiple tooth receiving/storage receptacle, these three prior art references are incomplete.

Prior Art: Summary of U.S. Patent Tooth Receiving Receptacles

There is no known prior art which comprises the combination of a single tooth receiving receptacle (pillow toothbox) stored within a multiple tooth receiving receptacle with a removable device by which to record date of loss.

Prior Art: General Receptacles

Containers with multiple compartments such as those found in craft stores exist in the prior art. These are generally for the purpose of storing sewing or craft supplies. However, the compartments in these containers are too large for storing a single tooth. Additionally, these boxes do not generally include a smaller removable receptacle that would act as a pillow toothbox.

Pill boxes with a plurality of compartments, each with its own lid, exist. However, these compartments are generally designed to hold numerous pills and are, therefore, too large for a single tooth. A pill box with twenty large compartments would be much too large and inconvenient to store tiny baby teeth. Also, a pill box with each compartment having its own lid would be more complex to manufacture. Additionally, pill boxes do not include a smaller removable receptacle that would act as a pillow toothbox.

OBJECTS AND ADVANTAGES

Accordingly, several objects and advantages of my invention are listed below.

First, it is an object to provide a teeth storage container which contains a smaller receptacle for holding a single tooth to place under a child's pillow as well as a removable device by which to record the date of loss. My device provides all three.

Second, it is an object to provide a teeth storage container with removable pillow toothbox which is simple. When I slip into my child's bedroom to do the tooth/coin exchange, I want the procedure to be simple and quick. Parents are very busy these days and have little time to deal with complex tooth fairy kits which entail a complicated procedure involving special pillowcases, fairy dust, footprints, messages and teacups. The sudden appearance of coins in place of the tooth under the child's pillow is just as convincing as is the use of a kit when enacting the tooth fairy myth. My device is very simple as well as quick, convenient and easy to use.

Third, it is an object to provide a teeth storage container with removable pillow toothbox which is inexpensive to manufacture and eliminates parts in the prior art. Kits are complex with multiple, varied contents all requiring varied systems of manufacture. Additionally, prior art teeth storage containers with a multiplicity of parts, as well as complicated apparatuses disguised as another item are expensive to manufacture. My device eliminates parts in the prior art and is easy and inexpensive to manufacture since the main body is only one piece.

Fourth, it is an object to provide a teeth storage container with removable pillow toothbox which is inexpensive to purchase. Due to the size, simplicity and uncomplicated nature of my device, as well as the low cost of manufacture, my invention will be inexpensive. If I had ever seen this invention in a department store or drug store, I would have bought it without a moment's hesitation because of the novelty and low cost. My device is inexpensive to purchase.

Fifth, it is an object to provide a teeth storage container with removable pillow toothbox which is age appropriate. Though juvenile designs exist, the child will not receive the keepsake box with all twenty baby teeth until she is at least a teenager if the parent chooses to enact the tooth fairy myth. Therefore, a simple, classic, non-childish mature shape and design is necessary. My device is age appropriate with an interesting, attractive, mature design and shape.

Sixth, it is an object to provide a teeth storage container with removable pillow toothbox which is durable. Containers or devices to store baby teeth which are made out of cardboard or flexible plastic with envelopes or pockets are fragile and will not last nearly as long as molded plastic, wood or any other firm, solid material. My device is durable.

Seventh, it is an object to provide a teeth storage container with removable pillow toothbox which is small and portable. Storage and display devices which are designed to be hung on the wall or which are large and disguised as another item are not portable. Portability offers the advantage of flexibility of placement. My device is small and easily portable.

Eighth, it is an object to provide a teeth storage container with removable pillow toothbox which is marketable. Based upon my research, there is a wide open market for my device. I have never seen anything even remotely close to it in stores. It is difficult to watch one's child grow so fast and leave his babyhood and childhood behind. Saving baby teeth is one small way to hold onto those childhood memories just a little longer. Parents everywhere would be thrilled to finally have an appropriate, convenient means by which to store their child's baby teeth. Marketing slogans and packaging directed at parents' need to hold onto their memories would be very effective and salable. Additionally, there is an endless market for my invention. As long as there are people, there will be children losing teeth. My device is salable and marketable. It satisfies a demand and has a perpetual market which is not seasonal.

Ninth, it is an object to provide a teeth storage container with removable pillow toothbox which is novel. Though other patents for storing baby teeth exist, my device has several novel features, one of the most important being its inclusion of a pillow toothbox in a specifically designed storage compartment. In addition to other novel features, it is different in design and shape (elliptical oval with the large inner compartment wall forming an off centered elliptical oval). It is unique over other containers in that its compartment walls are slightly lower than the outer wall. My device is unique and novel.

Tenth, it is an object to provide a teeth storage container with removable pillow toothbox which also includes a uniquely removable device for recording the date of loss of each tooth. This disconnectablity distinction is a new feature not found in the prior art. Removability is a definite advantage because it allows the recording device to be copied for educational purposes. Parents may keep a permanent record on the original recording device, while children may enjoy keeping their own personal record on a copy. Photocopies are extremely inexpensive and may be replaced if lost. Additionally, teachers may make copies for all students when discussing teeth in health class, again attesting to its educational value. My device offers the new feature of a tooth loss date recording device which is removable.

Eleventh, it is an object to provide a containment device with removable receptacle which is so appealing and desirable that someone who sees one demonstrated by another person will want one too. Children, especially, want what their friends have, and the collector box with its pillow toothbox will be very popular. My device is appealing and desirable.

Twelfth, it is an object to provide a containment device with removable receptacle which is lightweight and small. Children love to own small lightweight containers with smaller things placed inside (i.e. treasure box). Additionally, it fits neatly inside a parent's or child's dresser drawer. My device is lightweight, compact and small.

Thirteenth, it is an object to provide a containment device with removable receptacle which is reliable, reusable, operable, of good quality and useful in its own right. The use of the invention does not depend on others. The quality is high; the product is inexpensive but not cheap. It is consistent, easy to operate and can be used again and again. My device has all five of the above characteristics.

Fourteenth, it is an object to provide a containment device with removable receptacle which satisfies an existing need. The invention can replace all the pill bottles, pouches, plastic soap dishes and cardboard jewelry boxes presently used to store baby teeth. My device fulfills an existing need.

Further objects and advantages of my invention will become apparent from a consideration of the drawings and ensuing description.

SUMMARY

The present invention comprises a collection/storage receptacle specifically designed for baby teeth. The receptacle contains a smaller single tooth receptacle in its own storage compartment, a removable device by which to record tooth loss, a shield and instructions.

DRAWINGS

Drawing Figures

The invention will be better understood and objects other than those set forth above will become apparent when consideration is given to the following detailed description thereof. Such description makes reference to the annexed drawings wherein.

Figure 1:
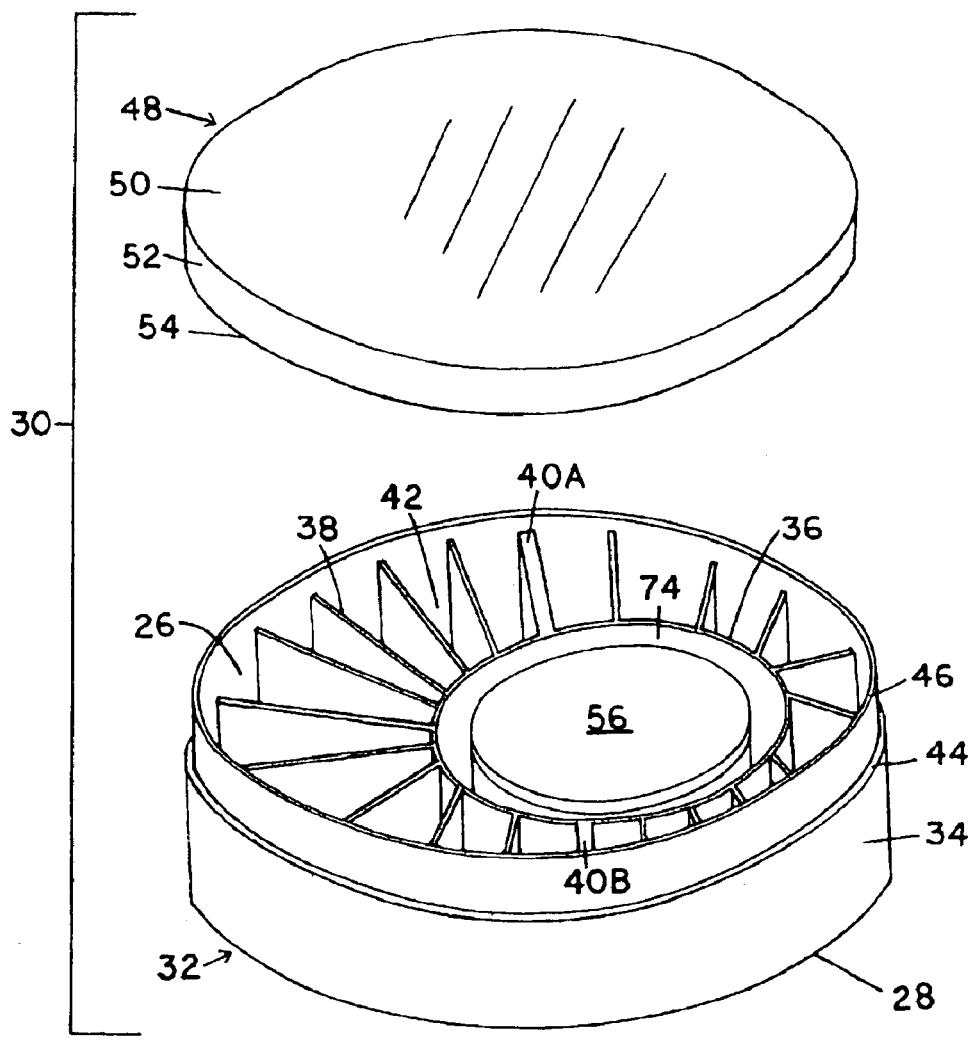
FIG. 1 is a front perspective view of open Baby Teeth Collector Box with Pillow Toothbox.

| Reference Numerals In Drawings | | | |
|---|---|---|---|
| 26 | Recess | 28 | Floor |
| 30 | Larger Receptacle | 32 | Body |
| 34 | Outer Sidewall | 36 | Inner Sidewall |
| 38 | Partition Walls | 40a, 40b | Double Partition Walls |
| 42 | Small Compartments | 44 | Ledge |
| 46 | Top edge | 48 | Cover |
| 50 | Cover base | 52 | Cover sidewall |
| 54 | Cover bottom edge | 56 | Removable Receptacle |
| 57 | R.R. recess | 58 | R.R. body |
| 59 | R.R. floor | 60 | R.R. outer sidewall |
| 62 | R.R. ledge | 64 | R.R. cover sidewall |
| 66 | R.R. cover | 68 | R.R. cover base |
| 70 | R.R. top edge | 72 | R.R. cover bottom edge |
| 74 | Large compartment | | |
| 82 | Diagram/date card | 84 | Instruction cards |
| 86 | Shield card | 88 | Upper baby teeth representation |
| 90 | Lower baby teeth representation | 92a | UPPER label |
| 92b | LOWER label | 94 | Date recording line |
| 95 | Tooth name labels | 96 | Openings |
| 98 | Outer edge | 100 | Centered oval body |
| 102 | Centered square body | 104 | Off centered square body |
| 106 | Centered triangle body | 108 | Centered Circle body |
| 110 | Off centered circle body | 112 | Centered pentagon body |
| 114 | Centered hexagon body | 116 | Centered ten-sided polygon body |
| 118 | Centered rectangle body | 120 | Off centered rectangle body |
| 122 | Asymmetrical rectangle body | 124 | Square/circle body |
| 126 | Star body | 128 | Transverse centerline |

DETAILED DESCRIPTION

Description—Preferred Embodiment

FIG. 1

FIG. 1 is a perspective view of the preferred embodiment of the invention. While it may take various configurations, it is preferably shaped as an elliptical oval. A larger receptacle 30 generally comprises a body 32 having an upwardly opening recess 26 with a floor 28 (shown clearly with hidden lines in FIG. 2) and a peripheral outer sidewall 34 upwardly extending from floor 28. Body 32 of larger receptacle 30 also comprises an inner sidewall 36, elliptically shaped and a little off centered, upwardly extending from floor 28.

Partition walls 38 and double partition walls 40a and 40b extend upwardly from floor 28 between outer sidewall 34 and inner sidewall 36 contiguous to each and forming a plurality of small compartments 42 along the perimeter of body 32 of larger receptacle 30. Partition walls 38 and double partition walls 40a and 40b all vary in length (the distance extending transversely from inner sidewall 36 to outer sidewall 34) due to the off centered positioning of elliptically shaped inner sidewall 36. (Also seen more clearly in FIG. 4)

Perferably there are twenty small compartments 42 to receive a child's twenty deciduous teeth. Small compartments 42 vary in size of necessity due to the off centered positioning of elliptically shaped inner sidewall 36. Each small compartment 42 is defined as small with respect to large compartment 74. All small compartments combined occupy approximately two thirds of body 32.

Double partition walls 40a and 40b are each twice the thickness of any single partition wall 38. This variation in wall thickness clearly divides the preferably twenty small compartments 42 into two sets of ten. One set of ten occupies slightly more than one half the perimeter of outer sidewall 34, and one set of ten occupies slightly less than one half the perimeter of outer sidewall 34; in other words, the two sets of ten do not make a definitive mirror image of one another.

Partition walls 38, double partition walls 40a and 40b and inner sidewall 36 are a little shorter than outer sidewall 34 in order to accommodate placement and storage of diagram/date card 82, instruction cards 84, and shield card 86 on top. (Cards 82, 84 and 86 are described later and shown in FIG. 5.)

A large compartment 74 formed within the inner periphery of inner sidewall 36 houses removable receptacle 56 which is described below and shown separately in FIG. 3. Large compartment 74 is defined as large with respect to small compartments 42. Large compartment 74 occupies approximately one third of body 32.

It is highly preferred that body 32 is formed as a single element, such as an integrally molded part (preferably plastic), so that the compartments are integrally connected and separation thereof is prevented.

At a distance of approximately two thirds to three fourths from floor 28 upward toward a top edge 46 of outer sidewall 34, outer sidewall 34 is reduced in thickness by approximately half and maintains the new thickness from that point to top edge 46. This change in thickness creates a ledge 44 upon which cover sidewall 52 will rest.

Larger receptacle 30 also comprises a cover 48. Cover 48 is, obviously, of the same shape as body 32 and comprises a cover base 50 and a peripheral cover sidewall 52 downwardly extending from base 50. Cover 48 slides onto body 32 with a friction fit and rests on ledge 44. The combined designs of ledge 44 and the change in thickness of outer sidewall 34 of body 32 allow cover sidewall 52 and outer sidewall 34 of body 32 to be flush when closed (showed in FIG. 2).

The distance from ledge 44 to top edge 46 of outer sidewall 34 of body 32 is equal to the distance from a cover bottom edge 54 of cover sidewall 52 to the interior side of cover base 50. This enables the interior side of cover base 50 to touch top edge 46 of outer sidewall 34 of body 32 when closed. This design produces a snug fit that allows contents to stay in their individual compartments when larger receptacle 30 is inverted.

FIG. 2

Figure 2:
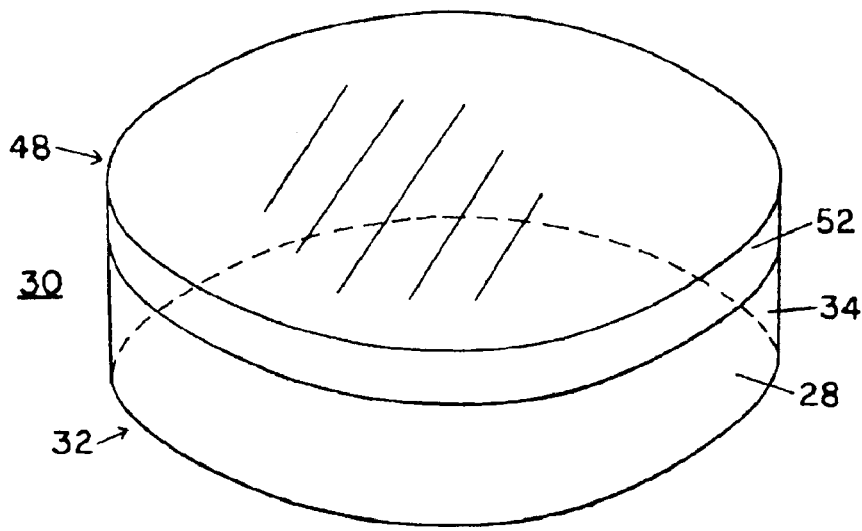
FIG. 2 is a front perspective view of the closed receptacle with hidden lines.

FIG. 2 is a perspective view of closed larger receptacle 30 comprising body 32 and cover 48. For more clarity, the only internal element illustrated here is floor 28, shown by hidden lines. Outer sidewall 34 of body 32 is shown flush with cover sidewall 52 as described above.

FIG. 3

Figure 3:
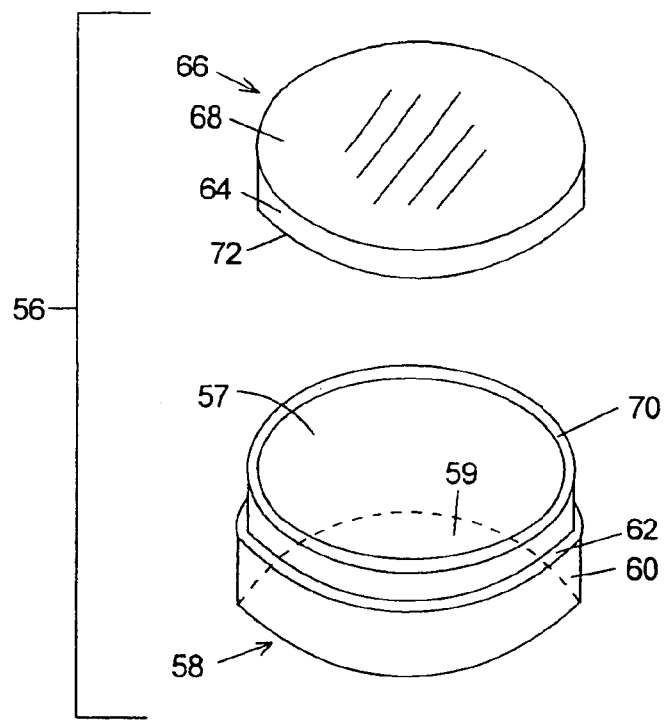
FIG. 3 is a front perspective view of the removable receptacle stored within the larger receptacle.

FIG. 3 is a perspective view of removable receptacle 56. (For simplification and clarity, the names of all removable receptacle 56 parts will begin with "R. R.") Its construction is much the same as larger receptacle 30 (FIG. 1). It is generally the same shape as larger receptacle 30 (preferably elliptical oval) and generally comprises an R.R. (removable receptacle) body 58 having an upwardly opening recess 57, with an R.R. floor 59 and a peripheral R.R. outer sidewall 60 upwardly extending from R.R. floor 59.

At a distance of approximately two thirds to three fourths from R.R. floor 59 upward toward an R.R top edge 70 of R.R. outer sidewall 60, R.R. outer sidewall 60 is reduced in thickness by approximately half and maintains the new thickness from that point to R.R. top edge 70. This change in thickness creates an R.R. ledge 62 upon which R.R. cover sidewall 64 will rest.

Removable receptacle 56 also comprises an R.R. cover 66. R.R. cover 66 is, obviously, of the same shape as R.R. body 58 and comprises an R.R. cover base 68 and a peripheral R.R. cover sidewall 64 downwardly extending from base 68. R.R. cover 66 slides onto R.R. body 58 with a friction fit and rests on R.R. ledge 62. The combined designs of R.R. ledge 62 and the change in thickness of R. R. outer sidewall 60 of R.R. body 58 allow R.R. cover sidewall 64 and R.R. outer sidewall 60 of R.R. body 58 to be flush when closed.

The distance from R.R. ledge 62 to R.R. top edge 70 of R.R. outer sidewall 60 of R.R. body 58 is equal to the distance from an R.R. cover bottom edge 72 of R.R. cover sidewall 64 to the interior side of R.R. cover base 68. This enables the interior side of R.R. cover base 68 to touch R.R. top edge 70 of R.R. outer sidewall 60 of R.R. body 58 when closed. This design produces a snug fit that allows contents to stay inside when removable receptacle 56 is inverted.

FIG. 3 AND FIG. 1

Returning to FIG. 1, removable receptacle 56 is stored in large compartment 74 of body 32 of larger receptacle 30; therefore, the perimeter of removable receptacle 56 is slightly less than that of the interior of inner sidewall 36.

The height of removable receptacle 56 does not exceed the height of inner sidewall 36 of body 32 of larger receptacle 30 when R.R. 56 is placed inside large compartment 74 of body 32. The interior height of removable receptacle 56 should be great enough to accommodate six to eight quarters.

It is preferred that removable receptacle 56 and larger receptacle 30 be made of molded opaque plastic. However, any number of other materials may be used.

FIG. 4

Figure 4:
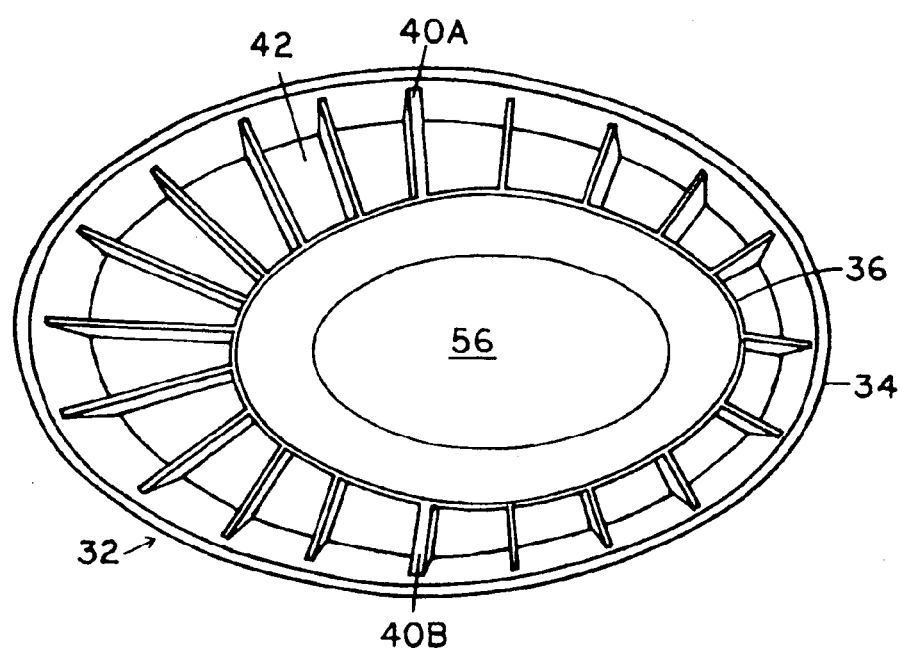
FIG. 4 is a top perspective view of the open body of the larger receptacle including the removable receptacle within.

FIG. 4 is a top perspective view of body 32 of the preferred embodiment of the invention and includes Removable Receptacle 56. FIG. 4 clearly shows inner sidewall 36 as being an ellipsis which is positioned off center to outer sidewall 34. Double partition walls 40a and 40b clearly divide the preferably twenty small compartments 42 into two sets of ten. The set of ten to the right occupies slightly more than one half the perimeter of outer sidewall 34, and the set of ten to the left occupies slightly less than one half the perimeter of outer sidewall 34; in other words, the two sets of ten do not make a definitive mirror image of one another.

FIG. 5

Figure 5:
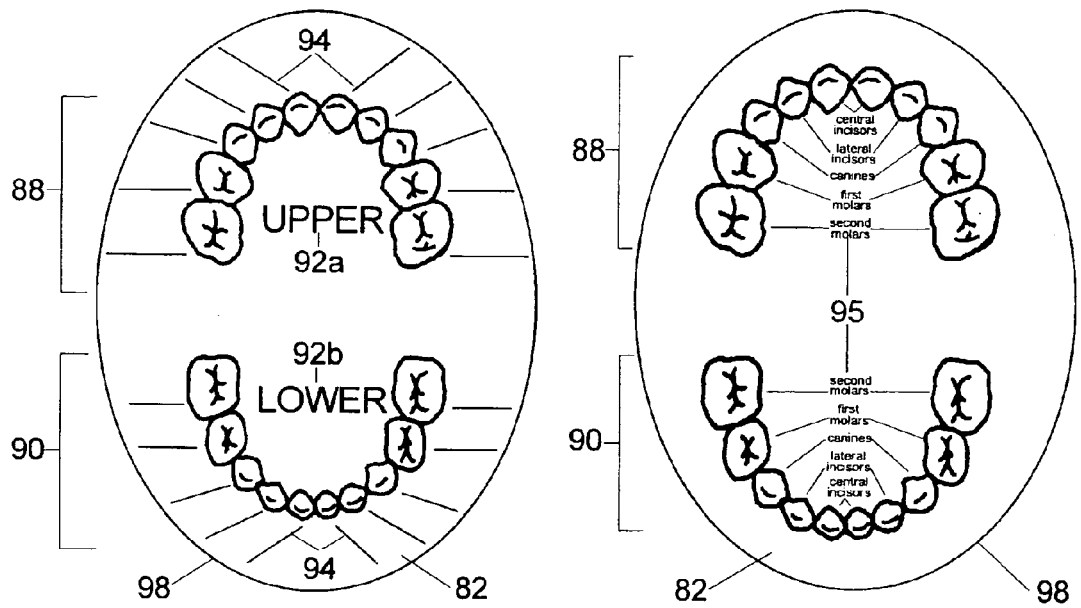
FIG. 5 is a top plan view of the cards contained within the invention (i.e. diagram/date card, shield card, and instruction cards).
Figure 5:
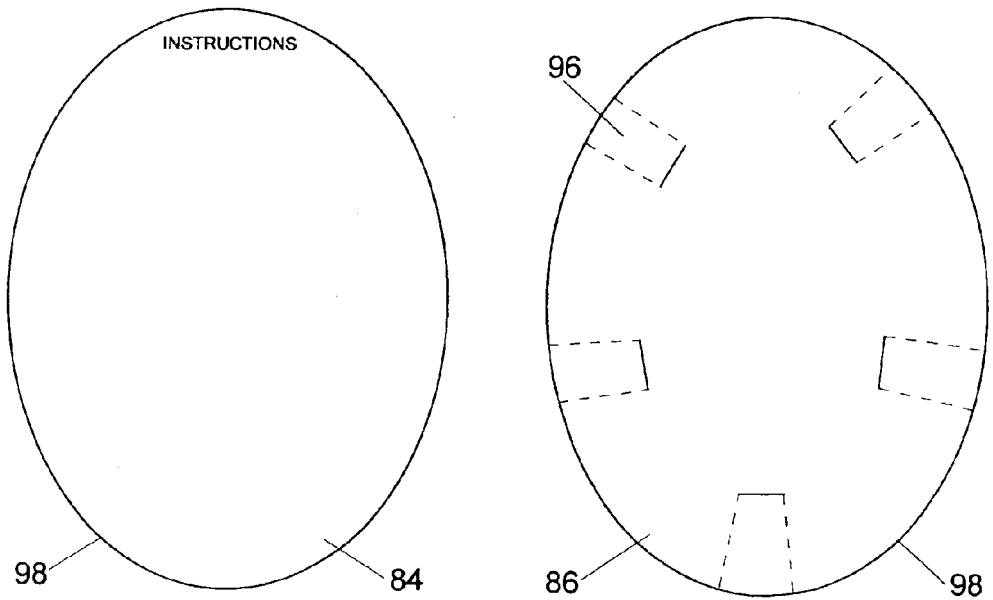

FIG. 5 is a top plan view of the cards which rest atop inner sidewall 36, partition walls 38 and center partition walls 40a and 40b of body 32 of larger receptacle 30 (FIG. 1). They include diagram/date card 82, instruction cards 84, and shield card 86. When stored, peripheral outer edges 98 of cards 82, 84 and 86 fall approximately 1 mm to 2 mm ($\frac{1}{16}$") from the peripheral of the interior side of outer sidewall 34. In other words, the perimeter of cards 82, 84, and 86 is slightly less than the perimeter of the interior of outer sidewall 34.

Diagram/date card 82 is removable for educational copying purposes and comprises graphical representations of the top surface of each baby tooth as they are aligned in the human jaw. Upper baby teeth representation 88 portrays upper teeth in a downward U-shaped arch and bears an "UPPER" label 92a. Lower baby teeth representation 90 portrays lower teeth in an upward U-shaped arch and bears a "LOWER" label 92b. In addition, a date recording line 94 is drawn adjacent to each of the twenty teeth displayed in graphical representations 88 and 90.

The reverse side of diagram/date card 82 also displays upper baby teeth representation 88 and lower baby teeth representation 90. Each tooth in representations 88 and 90 is identified by tooth name labels 95 which include the following: central incisors, lateral incisors, canines, first molars, and second molars.

The instructions written on instruction cards 84 are described in detail under "Operation".

Shield card 86 is to be used in symmetrical mirror image alternative embodiments. Its description and operation are given below under "Alternative Embodiments".

FIG. 6

Figure 6:
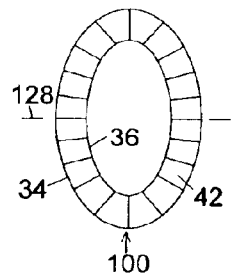
FIG. 6 shows simplified top plan views of numerous additional alternative embodiments.
Figure 6:
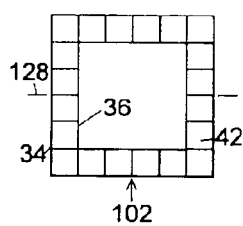
Figure 6:
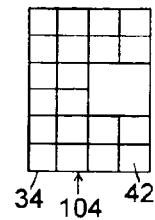
Figure 6:
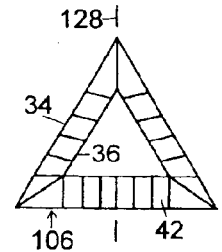
Figure 6:
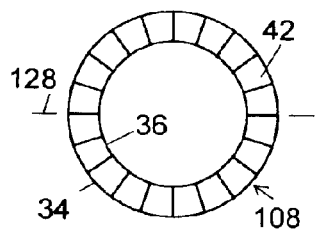
Figure 6:
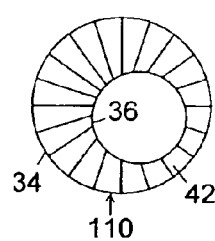
Figure 6:
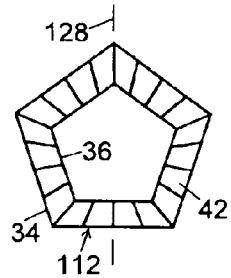
Figure 6:
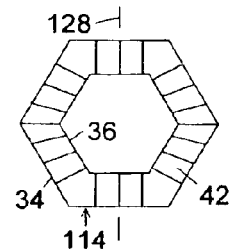
Figure 6:
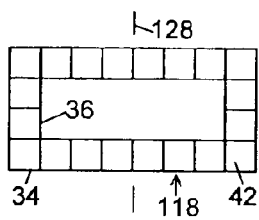
Figure 6:
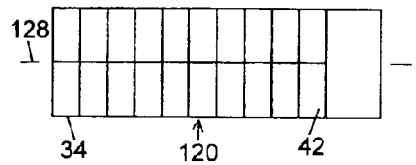
Figure 6:
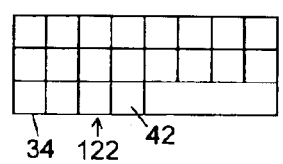
Figure 6:
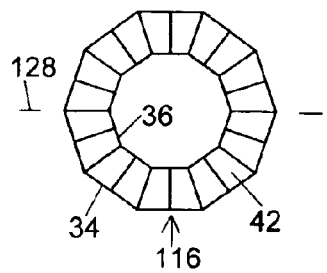
Figure 6:
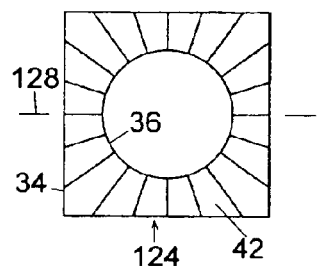
Figure 6:
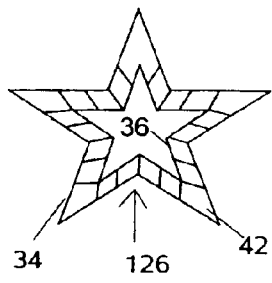

FIG. 6 shows simplified top plan views of the body of numerous alternative embodiments of the present invention. Their description and operation are given below under "Alternative Embodiments".

Operation—Preferred Embodiment

The operation of the preferred embodiment is very simple. Larger receptacle 30 (FIG. 1) may be used to store a child's twenty baby teeth. As each tooth becomes available, it is to be placed inside the compartment 42 which corresponds to the position in the child's jaw from whence it came. Compartments 42 are not perfectly symmetrical, nor mirror images, nor do ten compartments lie exactly in each half of body 32 of larger receptacle 30. However, the placement of the twenty compartments 42 in the oval shaped body 32 is close enough in similarity to representations 88 and 90 on diagram/date card 82 (FIG. 5) as to be able to clearly recognize which compartment 42 corresponds to which tooth. Double partition walls 40a and 40b drawn a clear distinction between each group of ten.

Small compartments 42 in the left portion of body 32 (FIG. 1) will serve to store teeth from the upper jaw, and small compartments 42 in the right portion of body 32 will serve to store teeth from the lower jaw. (The manufacturer may chose to place indicia "UPPER" and "LOWER" on the interior floor 28 of body 32 similar to UPPER label 92a and LOWER label 92b on diagram/date card 82.)

As each tooth is placed in its appropriate corresponding small compartment 42, the date of loss is to be recorded on the corresponding date recording line 94 on diagram/date card 82 (FIG. 5). Diagram/date card 82 is removable so that a parent or teacher may copy it for educational purposes. Card 82 is an excellent source for teaching the names and positions of baby teeth.

If the parent chooses to enact the tooth fairy fable, larger receptacle 30 will be secretly stored by the parent. If the parent chooses not to enact the tooth fairy fable, larger receptacle 30 may be given to the child to place on his dresser or shelf for display. It will be fun for him to watch it fill up with teeth, to record each date of loss, and to identify each tooth. Removable receptacle 56 (FIG. 3) may serve as a "Pillow Toothbox". This means the child may place her single tooth in the pillow toothbox in order to securely place it under her pillow for the tooth fairy. The tooth fairy then removes the tooth from R.R. 56, replaces it with coins, and then returns R.R. 56 to its place under the child's pillow. The child discovers and removes the coins in the morning. She may keep R.R. 56 singly in a safe place such as a dresser drawer, or in large compartment 74 of body 32 of larger receptacle 30 (FIG. 1) as decided by the parent.

Cover 48 (FIG. 1) and R.R. cover 66 (FIG. 3) are designed with a snug friction fit. This design facilitates easy removal by a child, but the fit is not so loose that cover 48 or R.R. cover 66 will fall off if receptacles 30 or 56 are inverted. Instruction cards 84 contain the following instructions:

1. Spread a cotton ball inside the smaller container (pillow toothbox) to act as a little cushion and muffler of clicking coins.
2. Child places single lost tooth on cottonball inside the pillow toothbox and positions toothbox under her pillow.
3. Tooth Fairy exchanges coins for the tooth and places the tooth in the appropriate corresponding compartment in the collector box. (The compartments are not perfectly symmetrical, but the double walls dividing the 20 compartments into two sets of ten will clearly indicate the correct placement of all teeth from upper and lower jaws.)
4. Record the date of loss on the line next to the corresponding tooth on Diagram/date card.
5. Tooth fairy hides the collector box until all 20 teeth are collected. Then the Pillow Toothbox is returned to its own compartment in the box and presented to the grown child. If there is no tooth fairy at your house, the collector box may be kept by the child and displayed in his room. The pillow toothbox may be used to store other "treasures".
6. To retrieve a single tooth for viewing, place a portion of cotton ball in all other compartments containing a tooth. Now the box may be turned upsidedown without all the teeth falling out and mixing. Tweezers may also be used.

Description—Alternative Embodiments

FIG. 6

FIG. 6 shows simplified top plan views of the body of numerous alternative embodiments.

In order to simplify, all walls are drawn with a single thin line rather than two to demonstrate thickness. One having ordinary skill in the art will understand that all simplified drawings in FIG. 6 are meant to show possible different shapes of the body and that they are built in essentially the same way as the preferred embodiment.

The present invention could be made in an infinite number of geometric shapes with a multitude of different arrangements of compartments. These include but are by no means limited to the following shown in FIG. 6: centered oval body 100, centered square body 102, off centered square body 104, centered triangle body 106, centered circle body 108, off centered circle body 110, centered pentagon body 112, centered hexagon body 1 14, centered ten-sided polygon body 116, centered rectangle body 118, off centered rectangle body 120, asymmetrical rectangle body 122, square/circle body 124, and star body 126.

The alternative embodiments' covers (not shown) would, of necessity, be the same outer peripheral shape as the body. Their removable receptacle (not shown) would most likely, but not necessarily be the same shape. It also may be possible to have an inner sidewall 36 which is a different shape from outer sidewall 34 (ex: square/circle body 124).

Transverse centerline 128 divides centered bodies 100, 102, 106, 108, 112, 114, 116, 118, 124 as well as off centered rectangle body 120 into halves. The bodies are symmetrical and each half is a mirror image of the other. Each half contains ten small compartments 42.

FIG. 5

FIG. 5 includes shield card 86 which relates only to symmetrical alternative embodiments having their preferably twenty small compartments 42 placed around the perimeter of the body and whose halves are mirror images of each other (ex: centered oval body 100, FIG. 6). The shape of shield card 86 will, of necessity, match the outer sidewall 34 alternative shape.

Shield card 86 portrays graphical representation of five openings 96 which correspond to every fourth compartment in an alternative body. (FIG. 5 shows shield card 86 which would be used for alternative oval body 100). Graphical representation of each opening 96 comprises a set of dotted lines drawn from outer edge 98 to a distance equal to the width of small compartments 42 and joined at that point by a solid line. Instructions for purpose and use are indicated on the back of shield card 86 and will be explained in the Operation portion below.

Operation—Alternative Embodiments

The alternative embodiments in FIG. 6 operate the same way as the preferred embodiments However, one additional feature is described here.

Shield card 86 (FIG. 5), for symmetrical alternative embodiments, has a unique design and serves a very useful purpose. After the teeth are placed inside the alternative symmetrical body, someone may wish to remove only one to view it. Shield card 86 was designed for the purpose of allowing the body to be turned upsidedown and to remove only one tooth without all of the teeth falling out. The dotted lines of openings 96 are meant to be cut by the parent. Then, the tab created by the cuts is to be folded back along the solid line. Placing shield card 86 on top of the body and then turning the body upsidedown with only one tab open, will release the desired tooth.

Shield card 86 is to be made of material stiff enough (preferably cardboard) such that the tab may be positioned back in its original place and another tab may be opened and used without the first tab opening and releasing a tooth. (Baby teeth weigh very little, so release of more than one tooth at a time should not be a problem.)

Understanding that most symmetrical mirror image alternative embodiment's body and shield card 86 are made up of four identical quadrants, only five rather than twenty openings 96 need to be cut. Openings 96 are specifically designed to be placed at every fourth small compartment 42. In this manner, an opening corresponding to each of the twenty compartments may be found by reversing or inverting shield card 86. This very simple design for retrieving a single tooth was specifically chosen to be in keeping with maintaining a low cost of manufacture and purchase.

Conclusion, Ramifications, and Scope

Thus the reader will see that the present invention provides a new device which is simple, convenient, durable, small, portable, marketable, salable, novel, unique, educational, lightweight, appealing, desirable, reliable, reusable, operable, interesting, and age appropriate. It eliminates parts in prior art, combines previously uncombined features, fulfills an existing need, and satisfies a demand having a perpetual market which is not seasonal. It is easy to use, inexpensive to manufacture and purchase, and useful in its own right.

It is a quality product with an attractive design and shape. It provides a device necessary to keep the ultimate memories of childhood: baby teeth. In short, the present invention abounds with advantages and is certainly needed.

While my above description contains many specificities, these should not be construed as limitations on the scope of the invention, but rather as an exemplification of one preferred embodiment and many sample alternative embodiments thereof Many other variations are possible. Some are listed below.

Alternative features and ramifications include but are not limited to the following:

- The invention's cover could be attached by hinges or other mechanism which allows the cover to move between open and closed positions. Such a cover could also require a mechanism or device such as but not limited to a clasp, spring, hook or other closure apparatus which would keep the cover closed.
- The inner sidewall and partition walls could be the same height as the outer sidewall. In this case, however, the cover would be redesigned with an open space between the top of the walls and the interior side of the cover to allow for placement of instruction, shield or diagram cards on top.
- Outer sidewall 34 could be the same thickness its entire height, thus eliminating ledge 44. In this case, cover sidewall 52 of a cover with a friction fit would simply overlap outer sidewall 34 and the two would not be flush.
- The body could be made in an infinite number of geometric shapes with its inner sidewall preferably but not necessarily matching in shape. The shape of the inner sidewall would determine the shape of the large compartment and, logically but not necessarily, the removable receptacle.
- The small compartments could be placed in a vast number of different arrangements within the body.
- The pillow toothbox and diagram/date card may be manufactured singly as "spare replacement parts" in the event they are lost. The collector box, however, would not be manufactured without the pillow toothbox or diagram/date card.
- The body could be made a different size.
- Materials other than molded plastic such as other synthetic material, wood or glass could be used.
- Shield card 86 could be varied in design or provide for more than five openings.
- Indicia may be placed on 3D shape pieces.

Accordingly, the scope of the invention should be determined not by the embodiments illustrated, but by the appended claims and their legal equivalents.

I claim:

1. A containment device for receiving articles selected from the group consisting of baby teeth and other objects of similar value, comprising in combination:
   (a) a body having an upwardly opening recess,
   (b) first means for dividing said recess into a plurality of compartments whereby baby teeth may be conveniently and organizationally stored,
   (c) second means for recording date of loss of each tooth, said second means being removably disposed in said recess of said body whereby said second means may be copied for educational purposes, and
   (d) third means for creating complete closure of said recess in said body and further defining said third means
      (1) comprising a cover selectively movable between positions opening and closing said recess, and further defining said cover as
      (2) covering and enclosing said second means within said body when said second means is disposed in said body.

2. The containment device of claim 1 wherein
   (a) the majority of said compartments are small with respect to the minority of said compartments, each one of said small compartments having a size of approximately one twentieth of two thirds of said body,
   (b) one of said compartments is large with respect to one of said small compartments of said majority, having a size of approximately one third of said body, and further including,
   (c) a receptacle being housed and removably disposed in said large compartment whereby a child may place a single tooth under her pillow.

3. The containment device of claim 2 wherein said removably disposed receptacle comprises:
   (a) a body having an upwardly opening recess, and
   (b) a cover selectively movable between positions opening and closing said recess whereby a single baby tooth or compensation may be enclosed within said recess.

4. The containment device of claim 3 wherein an inner sidewall and all compartment walls are slightly shorter than an outer sidewall whereby said second means for recording date of loss of each tooth may be conveniently placed on top of said walls and secured within a periphery of said outer sidewall.

5. The containment device of claim 4 wherein said outer sidewall of said body comprises a ledge approximately two thirds to three fourths of the distance upward from the bottom of said outer sidewall upon which said cover rests with a friction fit whereby said cover and said outer sidewall are flush thereby creating a clear-cut uniform appearance.

6. The containment device of claim 5 wherein said inner sidewall is positioned off centered thereby producing an asymmetrical arrangement of all said compartments.

7. The containment device of claim 6 wherein the outer periphery of a floor and said outer sidewall defines the shape of an elliptical oval.

8. The containment device of claim 5 wherein said inner sidewall is symmetrically centered in said body thereby producing
   (a) a symmetrical arrangement of all said compartments whereby said body may be balanced in form,
   (b) an imaginary averse centerline dividing said body into halves, said halves of said body being mirror images of one another, and
   (c) each said half containing ten said compartments whereby baby teeth may be logically placed.

9. The containment device of claim 8 further including fourth means for removing a single tooth for viewing, comprising a shield card
   (a) made in the same shape as said periphery of said outer sidewall of said body,
   (b) bearing graphical lines representing and corresponding to every fourth said small compartment whereby said lines may be cut creating an opening, and
   (c) whereby said shield card may be placed on top of said compartment walls and said containment device may be inverted thereby releasing a single tooth.

* * * * *